US006824793B1

(12) United States Patent
O'Hagan et al.

(10) Patent No.: US 6,824,793 B1
(45) Date of Patent: Nov. 30, 2004

(54) USE OF HYALURONIC ACID POLYMERS FOR MUCOSAL DELIVERY OF VACCINE ANTIGENS AND ADJUVANTS

(75) Inventors: Derek O'Hagan, Berkeley, CA (US); Alessandra Pavesio, Padua (IT)

(73) Assignees: Chiron Corporation, Emeryville, CA (US); Fidia Advanced Biopolymers Srl, Brindisi (IT)

( * ) Notice: Subject to any disclaimer, the term of this patent is extended or adjusted under 35 U.S.C. 154(b) by 0 days.

(21) Appl. No.: 09/724,661

(22) Filed: Nov. 28, 2000

Related U.S. Application Data

(60) Provisional application No. 60/087,596, filed on Jun. 1, 1998.

(51) Int. Cl.[7] .................................................. A61K 9/16
(52) U.S. Cl. ........................ 424/491; 424/489; 424/490; 424/497; 424/183.1; 424/184.1; 424/186.1; 424/193.1; 424/206.1; 424/278.1; 424/279.1
(58) Field of Search ................................ 424/489, 490, 424/491, 497, 183.1, 184.1, 186.1, 193.1, 206.1, 278.1, 279.1

(56) References Cited

U.S. PATENT DOCUMENTS

| 3,891,570 A | | 6/1975 | Fukushima et al. |
| 4,851,521 A | | 7/1989 | della Valle et al. |
| 4,965,353 A | | 10/1990 | della Valle et al. |
| 5,707,644 A | | 1/1998 | Illum |
| 5,900,238 A | * | 5/1999 | Gombotz et al. ......... 424/184.1 |

FOREIGN PATENT DOCUMENTS

| EP | 0216 459 B1 | 4/1987 |
| EP | 0 517 565 A3 | 12/1992 |
| EP | 0433 133 B1 | 3/1995 |
| WO | WO 95/17211 | 6/1995 |
| WO | WO 96/29998 | 10/1996 |
| WO | WO 97/07833 | 3/1997 |

OTHER PUBLICATIONS

Harlow et al. *Antibodies: A Laboratory Manual.* N.Y., Cold Spring Harbor, 1988. pp. 96–97. QR186.7.A53.*
Benedetti et al., "Microspheres of Hyaluronic Acid Esters—Fabrication Methods and In Vitro Hydrocortisone Release," *Journal of Controlled Release* 13:33–41 (1990).
Cortivo et al., "In Vitro Studies on Biocompatibility of Hyaluronic Acid Esters," *Biomaterials* 12:727–730 (1991).
Ghezzo et al., "Hyaluronane Derivative Microspheres as NGF Delivery Devices: Preparation Methods and In Vitro Release Characterization," *International Journal of Pharmaceutics* 87:21–29 (1992).

Illum et al., "Hyaluronic Acid Ester Microspheres as a Nasal Delivery System for Insulin," *Journal of Controlled Release* 29:133–141 (1994).
Koichiro, "Vaccine for Rhinovaccination," Japanese Abstract Pub. No. 05163161 (1993).
Kyyronen et al., "Methylprednisolone Esters of Hyaluronic Acid in Ophthalmic Drug Delivery:In Vitro and In Vivo Release Studies," *International Journal of Pharmaceutics* 80:161–169 (1992).
Longenecker et al., "Effects of Sodium Taurodihydrofusidate on Nasal Absorption of Insulin in Sheep," *Journal of Pharmaceutical Sciences* 76(5):351–355 (1987).
O'Hagan et al., "The Preparation and Characterization of Poly(lactide–co–glycoside) Microparticles: III Microparticle/Polymer Degradation Rates and the In Vitro Release of a Model Protein," *International Journal of Pharmceutics* 103:37–45 (1994).
Pritchard et al., "Evaluation of the Bioadhesive Properties of Hyaluronan Derivatives: Detachment Weight and Mucociliary Transport Rate Studies," *International Journal of Pharmaceutics* 129:137–145 (1996).
Richardson et al., "Novel Vaginal Delivery Systems for Calcitonin: I. Evaluation of HYAFF/Calcitonin Microspheres in Rats," *International Journal of Pharmaceutics* 115:9–15 (1995).
Richardson et al., "Gamma–Scinitraphy as a Novel Method to Study the Distribution and Retention of Bioadhesive Vaginal Delivery System in Sheep," *Journal of Controlled Release* 42:133–142 (1996).
Sharif and O'Hagan, "A Comparison of Alternative Methods for the Determination of the Levels of Proteins Entrapped in Poly(Lactide–Co–Glycoside) Microparticles," *International Journal of Pharmaceutics* 115:259–263 (1995).
Partidos et al., "The Adjuvant Effect of a Non–Toxic Mutant of Heat–Labile Enterotoxin of *Escherichia coli* for the Induction of Measles Virus–Specific CTL Responses After Intranasal Co–immunization with a Synthetic Peptide," *Immunology* 89:483–487 (1996).
Singh et al., "A Novel Bioadhesive Intranasal Delivery System for Inactivated Influenza Vaccines", J. Control Release, 70:267–276 (2001).

* cited by examiner

*Primary Examiner*—Jeffrey Stucker
(74) *Attorney, Agent, or Firm*—Roberta L. Robins; Michael J. Moran; Robert P. Blackburn

(57) ABSTRACT

Compositions are provided which include hyaluronic acid derivatives in combination with vaccine antigens, and optionally adjuvants, for mucosal delivery. Also provided are methods of making the compositions, as well as methods of immunization using the same.

15 Claims, 2 Drawing Sheets

USE OF HYALURONIC ACID POLYMERS FOR MUCOSAL DELIVERY OF VACCINE ANTIGENS AND ADJUVANTS

CROSS REFERENCE TO RELATED APPLICATIONS

This applications claims priority under 35 U.S.C. §365(c) and 35 U.S.C. §120 to PCT/US99/12105 and priority under 35 U.S.C. §119(e) to provisional application Ser. No. 60/087,596 filed Jun. 1, 1998.

TECHNICAL FIELD

The present invention relates generally to bioadhesive polymer systems. In particular, the invention relates to the use of hyaluronic acid polymers for mucosal delivery of vaccine antigens and adjuvants.

BACKGROUND OF THE INVENTION

Mucosal immunity provides an important defense mechanism against a wide variety of pathogens. In this regard, the mucosal surfaces of the gastrointestinal, respiratory and genitourinary tracts are continuously exposed to foreign antigens, including potentially infectious bacterial, vial and sometimes parasitic organisms. Mucosal immune responses protect against such challenges and have distinct and specialized characteristics.

For example, the principal immunoglobulin produced by the mucosal immune system is secretory IgA. Specialized antigen uptake cells in the Peyer's Patches of intestinal tract or nasopharyngeal lymphoid tissues, termed microfold or M cells, transport antigen to the underlying mucosal associated lymphoid tissues (MALT). In other areas of the mucosal epithelium, such as the pseudo-stratified airway epithelium, dendritic cells serve as antigen-presenting cells and migrate to local lymph nodes or MALT. Antigen processing and presentation occurs in the MALT, resulting in activation of antigen-specific IgA B cells. The subsequent trafficking and recirculation of the activated IgA-B cells to other components of the mucosal immune system, e.g., the respiratory, intestinal and genital tracts, provides for disseminated local mucosal IgA responses throughout the "Common Mucosal System." Thus, the mucosal immune system is uniquely suited to respond to the types of antigenic challenge encountered by mucosal surfaces and may provide the most effective type of immune response against particular pathogens. Accordingly, antigen delivery mechanisms which target the mucosal immune system provide an attractive means for achieving immunity.

Attempts have been made to use bioadhesive polymers for the mucosal delivery of drugs. Bioadhesives are synthetic and naturally occurring materials able to adhere to biological substrates for extended time periods. For example, Carbopol and polycarbophil, both synthetic cross-linked derivatives of poly(acrylic acid), display excellent adhesion properties in vitro. However, performance of these bioadhesives has not been duplicated in vivo. Additionally, such bioadhesives may cause local irritation. Hence, few bioadhesive delivery systems are commercially available.

Attention has therefore turned to the development of bioadhesive delivery systems based on naturally occurring substances, such as lectins and fimbrial proteins. These bioadhesives adhere to mucosal cell surfaces via receptor-mediated mechanisms. Another natural bioadhesive is hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Hyaluronic acid has been shown to be bioadhesive both in vivo and in vitro.

Esterified derivatives of hyaluronic acid have been used to produce microspheres that are biocompatible and biodegradable. See, e.g., Cortivo et al., *Biomaterials* (1991) 12:727–730; European Publication No. 517,565. These microspheres have been used for the mucosal delivery of a number of substances. See, e.g., International Publication No. WO 96/29998. For example, Richardson et al., *Int. J. Pharm.* (1995) 115:9–15), describe the vaginal delivery of calcitonin in rats. Additionally, Illum et al., *J. Controlled Rel.* (1994) 22:133–141 and European Publication No. 517, 565 describe the use of hyaluronic acid ester microspheres for the intranasal delivery of insulin in sheep.

However, the use of hyaluronic acid derivatives to deliver vaccine antigens has not heretofore been described.

DISCLOSURE OF THE INVENTION

The present invention provides an effective method for eliciting an immune response in a mammalian subject using mucosal immunization and hyaluronic acid delivery techniques. The present invention is based on the discovery that the mucosal delivery of hyaluronic acid derivatives, such as esterified hyaluronic acid polymers and auto-crosslinked hyaluronic acid polymers, in combination with an antigen of interest, and optionally an adjuvant, acts to enhance the immunogenicity of the antigen coadministered therewith. While not wishing to be bound by a particular theory, it is believed that the bioadhesive properties of the hyaluronic acid polymers decrease the rate of mucociliary clearance from the nasal cavity and thus allow a longer contact time between the antigen and the absorbing membrane. Additionally, a transient widening occurs at the tight junctions between the cells of the mucosal epithelia allowing more efficient transport of the antigen of interest. The use of hyaluronic acid polymers provides a safe and effective approach for enhancing the immunogenicity of a wide variety of antigens.

Accordingly, in one embodiment, the invention is directed to a composition comprising an hyaluronic acid ester polymer and a selected antigen, wherein the antigen is present in an amount of approximately 0.1% to about 40% (w/w) antigen to hyaluronic acid polymer.

In particularly preferred embodiments, the hyaluronic acid ester is selected from the group consisting of an hyaluronic acid where from about 75% to about 100% of free carboxyl groups are esterified with one or more alkyl groups, and a crosslinked derivative of hyaluronic acid in which about 0.5% to about 20% of the carboxyl groups of the hyaluronic acid polymer are crosslinked to hydroxyl groups of the same or a different hyaluronic acid molecule.

In another embodiment, the invention is directed to a composition comprising (a) a microsphere comprised of an hyaluronic acid ester selected from the group consisting of an hyaluronic acid where from about 75% to about 100% of free carboxyl groups are esterified with one or more alkyl groups, and a crosslinked derivative of hyaluronic acid comprising internal esters in which about 0.5% to about 20% of the carboxyl groups of the hyaluronic acid polymer are crosslinked to hydroxyl groups of the same or a different hyaluronic acid molecule; (b) a selected antigen entrapped in, or adsorbed to, the microsphere, wherein the antigen is present in an amount of approximately 2% to about 25% (w/w) antigen to hyaluronic acid polymer, and (c) an immunological adjuvant.

In still further embodiments, the subject invention is directed to methods of making pharmaceutical compositions which comprise combining the compositions above with pharmaceutically acceptable mucosal excipients, as well as methods of immunization comprising mucosally administering therapeutically effective amounts of the pharmaceutical compositions to a vertebrate subject.

These and other embodiments of the present invention will readily occur to those of ordinary skill in the art in view of the disclosure herein.

DETAILED DESCRIPTION OF THE INVENTION

Figure 1:
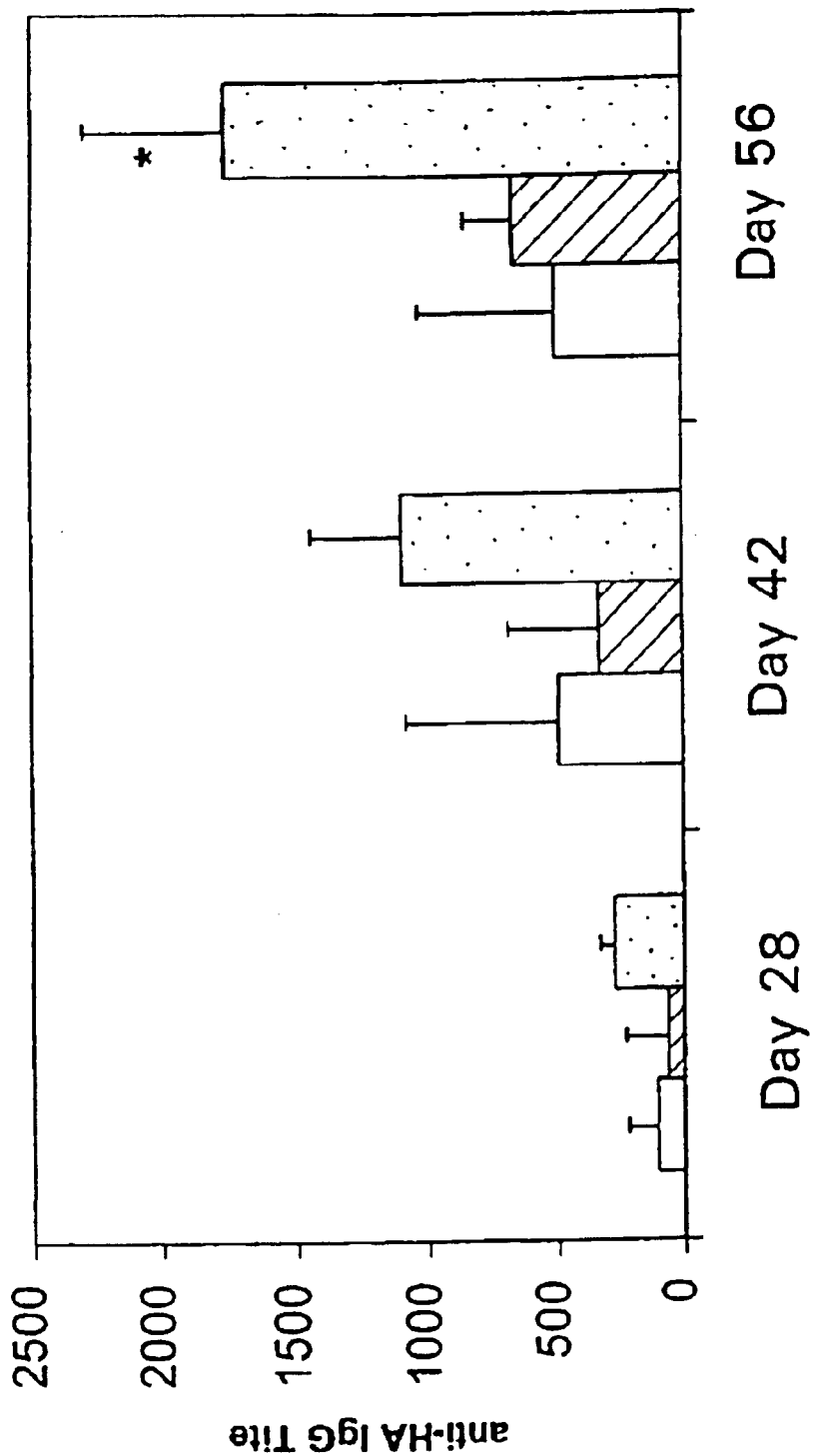
FIG. 1 shows anti-HA IgG titers in pigs administered HA alone intramuscularly (open bars), HA and the adjuvant LT-K63 intranasally (solid bars) and HA with HYAFF microparticles and LT-K63 intranasally (cross-hatched bars).

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I–IV (D. M. Weir and C. C. Blackwell, eds., 1986, Blackwell Scientific Publications); and Sambrook, et al., *Molecular Cloning: A Laboratory Manual* (2nd Edition, 1989).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

1. Definitions

In describing the present invention, the following terms will be employed, and are intended to be defined as indicated below.

The terms "hyaluronic acid" and "hyaluronan" are used herein to denote an art-recognized acidic polysaccharide which is an unbranched long-chain molecule made up of repeating monomeric units of D-glucuronic acid linked by a β1-3 glucosidic bond to N-acetyl-D-glucosamine (structure 1, below); a β1-3 glucosidic bond links the single units.

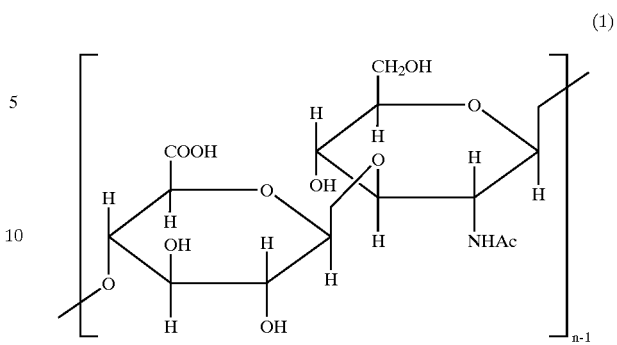

(1)

An "hyaluronic acid derivative" is a molecule derived from hyaluronic acid and denotes any of various substances, known in the art, such as esterified hyaluronic acid molecules wherein approximately 75%–100% of the free carboxyl groups are esterified with an alkyl group, collectively termed "HYAFF" herein. The term also includes "mixed" hyaluronic acid esters, wherein carboxyl groups are esterified with more than one alkyl group. Such "mixed" esters are described more fully below. Furthermore, the term "hyaluronic acid derivative" also refers to auto-crosslinked derivatives of hyaluronic acid, termed "ACP" herein, which include internal esters and in which about 0.5% to about 20% of the carboxyl groups of the hyaluronic acid polymer are crosslinked to hydroxyl groups of the same or different hyaluronic acid molecules. Such molecules are described in greater detail below.

The term "microsphere" as used herein, refers to an hyaluronic acid particle of about 100 nm to about 150 μm in diameter, more preferably about 200 nm to about 30 μm in diameter, and most preferably about 500 nm to about 10 μm in diameter. Microsphere size is readily determined by techniques well known in the art, such as photon correlation spectroscopy, laser diffractometry and/or scanning electron microscopy. Microspheres for use herein will be formed from hyaluronic acid polymers and derivatives thereof, described in more detail, that are non-toxic and biodegradable.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl, benzyl, and the like.

By "mucosal" delivery is meant delivery of an antigen to a mucosal surface, including nasal, pulmonary, vaginal, rectal, urethral, and sublingual or buccal delivery.

By "antigen" is meant a molecule which contains one or more epitopes that will stimulate a host's immune system to make a cellular antigen-specific immune response when the antigen is presented, or a humoral antibody response. Normally, an epitope will include between about 3–15, generally about 5–15, amino acids.

For purposes of the present invention, antigens can be derived from any of several known viruses, bacteria, parasites and fungi. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A vaccine composition which contains a selected antigen in combination with an hyaluronic acid polymer as described herein, displays "enhanced immunogenicity" when it possesses a greater capacity to elicit an immune response than the immune response elicited by an equivalent amount of the antigen without the hyaluronic acid polymer. Thus, a vaccine composition may display "enhanced immunogenicity" because the antigen is more readily absorbed by the vertebrate subject, or because the antigen is more strongly immunogenic or because a lower dose of antigen is necessary to achieve an immune response in the subject to which it is administered. Such enhanced immunogenicity can be determined by administering the polymer/antigen composition, and antigen controls to animals and comparing antibody titers against the two using standard assays such as radioimmunoassay and ELISAs, well known in the art.

The terms "effective amount" or "pharmaceutically effective amount" of an agent, as provided herein, refer to a nontoxic but sufficient amount of the agent to provide the desired immunological response and corresponding therapeutic effect. As will be pointed out below, the exact amount required will vary from subject to subject, depending on the species, age, and general condition of the subject, the severity of the condition being treated, and the particular antigen of interest, mode of administration, and the like. An appropriate "effective" amount in any individual case may be determined by one of ordinary skill in the art using routine experimentation.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "pharmaceutically acceptable" or "pharmacologically acceptable" is meant a material which is not biologically or otherwise undesirable, i.e., the material may be administered to an individual along with the microparticle formulations without causing any undesirable biological effects or interacting in a deleterious manner with any of the components of the composition in which it is contained.

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn subjects are intended to be covered. The system described above is intended for use in any of the above vertebrate species, since the immune systems of all of these vertebrates operate similarly.

II. Modes of Carrying Out the Invention

Before describing the present invention in detail it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention utilizes hyaluronic acid-mediated delivery techniques to elicit an immune response against mucosally transmitted pathogen. The system affords a vigorous immune response, even when the antigen is by itself weakly immunogenic. Although the individual components of the vaccine compositions and methods described herein were known, it was unexpected and surprising that such combinations would enhance the efficiency of antigens beyond levels achieved when the components were used separately.

Although the invention is broadly applicable for providing an immune response against any of the above-mentioned pathogens, the invention is exemplified herein by reference to influenza virus.

The method of the invention provides for cell-mediated immunity, and/or humoral antibody responses. Accordingly, the methods of the present invention will find use with any antigen for which cellular and/or humoral immune responses are desired, including antigens derived from viral, bacterial, fungal and parasitic pathogens that may induce antibodies, T-cell helper epitopes and T-cell cytotoxic epitopes. Such antigens include, but are not limited to, those encoded by human and animal viruses and can correspond to either structural or non-structural proteins.

For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI) and an N-terminal nucleocapsid protein (termed "core") (see, Houghton et al., *Hepatology* (1991) 14:381–388, for a discussion of HCV proteins, including E1 and E2). Each of these proteins, as well as antigenic fragments thereof, will find use in the present methods. Similarly, the sequence for the δ-antigen from HDV is known (see, e.g., U.S. Pat. No. 5,378,814) and this antigen can also be conveniently used in the present methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines— from the laboratory to license: a case study" in Mackett, M. and Williamson, J. D., *Human Vaccines and Vaccination*, pp. 159–176, for a discussion of HBV structure; and U.S. Pat. Nos. 4,722,840, 5,098,704, 5,324,513, incorporated herein by reference in their entireties; Beames et al., *J. Virol.* (1995) 69:6833–6838, Birnbaum et al., *J. Virol.* (1990) 64:3319–3330; and Zhou et al., *J. Virol.* (1991) 65:5457–5464.

Antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviddae; Arenaviridae; Retroviradae (e.g., HTLV-I; HTLV-II; HIV-1 (also known as HTLV-III LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope proteins from any of the above HIV isolates, including members of the various genetic subtypes of HIV, are known and reported (see, e.g., Myers et al., Los Alamos Database, Los Alamos National Laboratory, Los Alamos, N.Mex. (1992); Myers et al., *Human Retroviruses and Aids*, 1990, Los Alamos, N.Mex.: Los Alamos National Laboratory; and Modrow et al., *J. Virol.* (1987) 61:570–578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region. As explained above, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 12:759–767; Webster et al., "Antigenic variation among type A influenza viruses," p. 127–168. In: P. Palese and D. W. Kingsbury (ed.), *Genetics of influenza viruses*. Springer-Verlag, New York). Thus, proteins derived from any of these isolates can also be used in the immunization techniques described herein.

The methods described herein will also find use with numerous bacterial antigens, such as those derived from organisms that cause diphtheria, cholera, tuberculosis, tetanus, pertussis, meningitis, and other pathogenic dates, including, without limitation, *Meningococcus* A, B and C, *Hemophilus influenza* type B (HIB), and *Helicobacter pylori*. Examples of parasitic antigens include those derived from organisms causing malaria and Lyme disease.

Furthermore, the methods described herein provide a means for treating a variety of malignant cancers. For example, the system of the present invention can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993) :82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to prevent or treat a wide variety of diseases.

The selected antigen is combined with the hyaluronic acid polymer for subsequent mucosal delivery. Hyaluronic acid polymers for use in the subject compositions are available from, e.g., Fidia Advanced Biopolymers Srl (Abano Terme, Italy). For example, useful polymers in the methods described herein include, but are not limited to, esterified and auto-crosslinked derivatives of hyaluronic acid. These polymers are available in a variety of molecular weights, and the appropriate molecular weight for use with a given antigen is readily determined by one of skill in the art. Thus, e.g., for esterified derivatives, a suitable molecular weight will be on the order of about 2000 to 300,000, more preferably about 50,000 to about 250,000, even more preferably about 75,000 to about 200,000, and most preferably about 100,000 to about 150,000.

Particularly useful esterified forms of hyaluronic acid are those where approximately 75–100% of the carboxyl groups are esterified with an alkyl group such as an ethyl, propyl, pentyl benzyl, dodecyl and the like, formed by the reaction of free carboxyl groups with the corresponding alcohol. Such derivatives are particularly preferred due to their biocompatibility and their ability to biodegrade by hydrolysis of ester bonds. Residues which are not esterified with an alkyl group as above, may be reacted with lipid chain/alkyl residues from a $C_{10-20}$ aliphatic alcohol to produce "mixed" esters. In this embodiment, preferably 75% of the carboxyl groups are esterified with e.g., benzyl groups and at least about 5% of the remaining groups esterified with the aliphatic alcohol. See, e.g., International Publication No. WO 97/07833.

A representative structure for an esterified hyaluronic acid is shown below as structure 2, wherein R represents an alkyl group as described above.

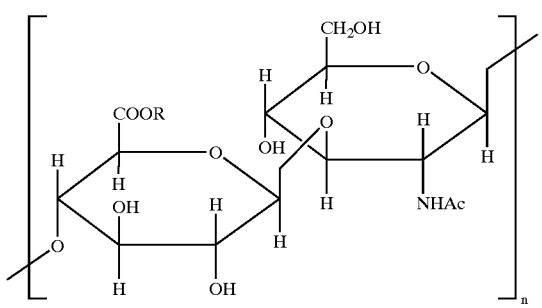

(2)

Such derivatives are described in, e.g., U.S. Pat. Nos. 4,851,521 and 4,965,353, and European Patent Publication No. 517,565 and are available from e.g., Fidia Advanced Biopolymers Srl (Abano Terme, Italy). Representative formulations include those known as: HYAFF7 (ethyl ester), HYAFF9 (propyl ester), HYAFF11 (benzyl ester), HYAFF21 (pentyl ester), HYAFF73 (dodecyl ester), and the like, which are approximately 100% esterified; and HYAFF11p50 (benzyl ester), HYAFF7p75 (ethyl ester), and HYAFF11p75 (benzyl ester), etc. which are approximately 50 to 75% esterified.

These derivatives are readily produced by reaction of the free carboxyl groups present in hyaluronic acid with an alcohol, in the presence of catalyzing substances, such as strong inorganic acids or ionic exchangers of the acid type, or with an etherifying agent capable of introducing the desired alcoholic residue in the presence of inorganic or organic bases. For example, a quaternary ammonium salt of hyaluronic acid may be treated with an etherifying agent, such as an aprotic organic solvent, as described in European Publication No. 216,453. See, also, European Publication No. 433,133 and U.S. Pat. Nos. 4,851,521 and 4,965,353, incorporated herein by reference in their entireties.

The degree and type of esterification can be varied, and are largely a matter of choice, depending in part on the coadministered antigen, the degree of bioadhesion desired, as well as the rate of delivery desired, as described in more detail below. A suitable percentage and type of esterification, is easily determined by one of skill in the art based on the nature of the antigen and disorder in question.

As explained above, the hyaluronic acid derivative known as ACP, will also find use for delivering vaccine antigens herein. Generally, ACPs for use with the present invention will be those where about 0.5 to about 20%, preferably about 3% to about 10%, and most preferably about 4% to about 5%, of the carboxyl groups of the hyaluronic acid polymer are crosslinked to hydroxyl groups of the same or different hyaluronic acid molecules. The remainder of the molecule may be salified. One preferable form of an ACP for use herein is a viscous, gel-like composition. See, e.g., International Publication No. WO 97/07883.

ACP derivatives are made by first activating hyaluronic acid having either free carboxyl groups or salted carboxyl groups, with an agent which activates the carboxyl function. Typical agents include carbodiimides, dicyclohexylcarbodiimide, benzylisopropylcarbodiimide, benzylethyl carbodiimide, ethoxyacetylene, halogen derivatives from aliphatic, cycloaliphatic or aromatic hydrocarbons, and the like. Auxiliary agents may be present which favor formation of intermediate activated derivatives and/or a tertiary organic or inorganic base, such as triethylamine.

Activation is carried out in an organic, aprotic solvent, such as in DMSO, and the mixture is exposed to heat or irradiation (particularly UV light). In this way, unstable intermediates are formed which separate spontaneously, either after the addition of catalysts and/or following a rise in temperature, thereby forming inner ester bonds with hydroxyls of the same or other hyaluronic acid molecules. See, e.g., European Publication No. 341,745 and International Publication No. WO 97/07883, for methods of producing these derivatives.

The hyaluronic acid derivatives described above can be provided as microspheres, either with adsorbed or physically incorporated (entrapped) antigen, using any of several techniques, well known in the art. For example, the microspheres can be made using solvent evaporation and extraction techniques. Generally, these methods entail the preparation of an emulsion of two unmixable liquids, called the discontinuous and continuous phases. The discontinuous phase includes microdroplets of polymer/solvent solution containing the antigen (if it is to be entrapped). The discontinuous phase is subsequently mixed with a continuous aqueous phase containing a particle stabilizer/surfactant. After the emulsion is stabilized, the discontinuous phase is removed by evaporation or extraction. See, e.g., Benedetti et al., *J. Controlled Rel.* (1990) 13:33–41; Ghezzo et al., *Int. J. Pharm.* (1992) 87:21–29; Illum et al., *J. Controlled Rel.* (1994) 29:133–141; European Publication No. 517,565.

More particularly, an appropriate hyaluronic acid derivative is dissolved in a solvent, the solvent selected such that it does not react chemically with the polymer or the antigen and is immiscible in the continuous phase. Any number of solvents can be used, such as, for example, an aprotic solvent including, but not limited to, dimethylsulfoxide (DMSO), 1,1,1,3,3,3-hexafluoro-2-propanol (HFIP), and the like. The polymer is added at a concentration of about 0.5% to about 10% w/v, preferably about 1% to about 8% w/v, and most preferably about 6% to about 8% w/v. Depending on the antigen used and the loading desired, an amount of antigen is added that will result in a microsphere with approximately 0.1% to about 40% (w/w) antigen to hyaluronic acid polymer, more preferably about 1% to about 25% (w/w) antigen, and even more preferably about 2% to about 20% (w/w) antigen. This mixture forms the discontinuous phase.

A continuous phase mixture is prepared which includes a second solvent, generally a high viscosity oil, such as heavy mineral oil or paraffin oil (Sigma Chemical Co., St. Louis, Mo.). An emulsion stabilizer is present, such as a nonionic surface active agent, including for example, mannide monooleate (Arlacel A®), dextran 70,000, polyoxyethylene ethers (Triton®), polyglycol ethers (Tergitol®), and the like, all readily commercially available from, e.g., Sigma Chemical Co., St. Louis, Mo. The surface active agent will be present at a concentration of about 0.3% to about 10%, preferably about 0.5% to about 8%, and more preferably about 1% to about 5%.

To produce microspheres, the discontinuous phase is then added to the continuous phase at a ratio of about 1:16, and an emulsion is formed by e.g., mechanical stirring at about 700 to 1000 rpm. Organic solvents are then evaporated or extracted. If evaporated, the emulsion temperature is kept below the solvent boiling point and gradually increased (still being maintained below the solvent boiling point) until the solvent is evaporated. See, e.g., U.S. Pat. No. 3,891,570 and Benedetti et al., *J. Controlled Rel.* (1990) 13:33–41.

If extracted, an appropriate extraction solvent, i.e., a solvent for the discontinuous phase solvent but not the hyaluronic acid derivative, is added to the emulsion in a ratio of about 2:1 v/v, and the solution is then stirred until microspheres are formed. For example, if DMSO is used, it can be extracted using ethyl acetate or acetyl acetate. Other appropriate extraction solvents can be readily determined by one of skill in the art. For a further description of the solvent extraction technique, see, e.g., Illum et al., *J. Controlled Rel.* (1994) 29:133–141; and Ghezzo et al., *Int. J. Pharm.* (1992) 87:21–29; and European Publication No. 517,565.

Once the dispersed phase solvent is removed, the suspended microspheres are separated from the oil phase by centrifugation. Microspheres can be resuspended in an appropriate solution, such as hexane, to remove excess mineral oil and surfactant, and the solution is then filtered. This process may be repeated a number of times to ensure removal of solvent. The microspheres are then air-dried or dried under vacuum.

Alternatively, microspheres can also be formed using spray-drying, as described in, e.g., Kyyronen et al., *Int. J. Pharm.* (1992) 80:161–169; Ghezzo et al., *Int. J. Pharm.* (1992) 87:21–29; and Masters, K. (1976) *Spray Drying* 2nd Ed. Wiley, New York. Especially small microspheres, termed "nanospheres" can be produced using supercritical antisolvents (SAS), as described in International Publication No. WO 96/29998.

Rate of release of the antigen from the hyaluronic acid compositions can be modified depending on the method used to associate the antigen with the microspheres. For example, if the antigen is physically dispersed in the polymer matrix, release is controlled largely by the diffusion rate of the antigen through the polymer network. Furthermore, if solvents are extracted rather than evaporated, microspheres include more porous surfaces which result in more rapid release of the entrapped antigen.

Furthermore, esterification of carboxyl groups reduces the bioadhesiveness of hyaluronic acid due to the reduced tendency for esters to form hydrogen bonds with the biological substrate. Additionally, the hydrophobicity of the microspheres, imparted by differing esters and degrees of crosslinking, will affect the amount of bioadhesion since mucosal tissue appears to display appreciable hydrophobicity which may have important implications for bioadhesion. Thus, for example, a higher degree of esterification generally gives rise to slower and reduced release of the entrapped protein but produces a microsphere with enhanced bioadhesive properties.

Additionally, biological factors such as ciliary beat frequency, as well as physical factors such as particle size, density and degree of clumping, and water solubility of the antigen, will influence the degree of bioadhesion and bioerosion See, e.g., Pritchard et al., *Int. J. Pharm.* (1996) 129:137–145.

Moreover, mixtures of microspheres with varying esters, varying amounts of esterification, as well as varying degrees of crosslinking, will find use in the formulations in order to achieve the desired bioadhesion and release kinetics for a given antigen and to provide for both a primary and secondary immune response.

Once formed, the adhesiveness of a particular hyaluronic acid/antigen combination may be determined using any number of methods, well known in the art, in order to assess whether a particular formulation has appropriate bioadhesive properties. For example, in vitro detachment weight studies can be conducted which are based on surface tension measurements. See, e.g., Smart et al., *J. Pharm. Pharmacol.* (1984) 36:295–299. Briefly, test microspheres are applied to a biological substrate, such as epithelial tissue, and detachment weight studies conducted using an apparatus that determines the weight required to detach two tissue sections from the test bioadhesive which is sandwiched between them. See, e.g., Pritchard et al., *Int. J. Pharm.* (1996) 129:137–145. Alternatively, mucociliary transport rate can be used as a determinant of adhesiveness since the greater the adhesiveness of the test substance, the slower the transport rate. Such studies can be conducted by, e.g., monitoring the movement of bioadhesives along part of an excised upper palate from the frog (*Rana pipiens*), as described in Pritchard et al., supra.

Similarly, the rate of bioerosion of the microspheres can be determined using standard techniques, well known in the art, such as by in vitro release profiles, to determine whether the hyaluronic acid/antigen formulation in question provides an adequate amount of antigen to the immune system for the given disease. For example, dissolution tests can be performed by e.g., dispersing microspheres in an appropriate buffer such as a phosphate buffer or BSA, with continuous stirring. Samples of the solution are removed at fixed time intervals and assayed for the antigen of interest using, e.g., ELISAs or any other appropriate assay. See, Ghezzo et al., *Int. J. Pharm.* (1992) 87:21–29.

Particle size can be determined by, e.g., laser light scattering, using for example, a spectrometer incorporating a helium-neon laser. Generally, particle size is determined at room temperature and involves multiple analyses of the sample in question (e.g., 5–10 times) to yield an average value for the particle diameter. Particle size is also readily determined using scanning electron microscopy (SEM). In order to do so, dry microspheres are sputter-coated with a gold/palladium mixture to a thickness of approximately 100 Angstroms, then examined using a scanning electron microscope.

If the antigen is provided in a microsphere, the antigen content is generally determined so that an appropriate amount of the microspheres may be delivered to the subject in order to elicit an adequate immune response. Antigen content can be determined according to methods known in the art, such as by disrupting the microspheres and extracting any entrapped antigen. For example, microspheres can be dissolved in a solvent such as DMSO or dispersed in, e.g., 0.1 M NaOH containing 5% (w/v) SDS. The sample is agitated, optionally centrifuged, and the supernatant assayed for the antigen of interest using an appropriate assay. See, e.g., Benedetti et al., *J. Controlled Rel.* (1990) 13:33–41; and O'Hagan et al., *Int. J. Pharm.* (1994) 103:37–45.

Alternatively, the hyaluronic acid derivatives, either in the form of microspheres or not, can be combined directly with antigen, rather than entrapping antigen therein, using any of several methods, well known in the art. For example, antigen can be adsorbed rather than entrapped in microspheres by mixing the antigen with the hyaluronic acid polymer in an appropriate buffer, incubating for varying periods of time, depending on the hyaluronic acid polymer used, and if desired, lyophilizing the formulation for future use. Thus, for example, if HYAFF or mixed ester derivatives are used, the antigen is generally incubated with the hyaluronic acid polymer in an amount that represents approximately 0.1% to about 40% (w/w) antigen to hyaluronic acid polymer, more preferably about 1% to about 25% (w/w) antigen, and even more preferably about 2% to about 20% (w/w) antigen. The percentage of antigen will depend on the desired dose and the condition being treated, as discussed in more detail below. Incubation of antigen with polymer will proceed for approximately 0 hours to 48 hours or more, preferably about 0 hours to about 24 hours, more preferably about 1 hour to about 10 hours, and most preferably about 2 hours to about 4 hours. Following incubation, the suspension can be lyophilized and the dried composition suspended in an appropriate vehicle prior to immunization.

If ACP is used, ACP can be provided as a gel, see, International Publication No. WO 97/07833 (available from Fidia Advanced Biopolymers Srl (Abano Terme, Italy). ACP gel is diluted 1:30 with saline and mixed with the antigen, and optionally an adjuvant (see further below). The solution can then be administered directly to the subject, e.g., intranasally, as discussed in more detail below.

Once the antigen and hyaluronic acid derivatives are made, as above, compositions are formulated for subsequent mucosal delivery. The compositions will generally include one or more "pharmaceutically acceptable excipients or vehicles" appropriate for mucosal delivery, such as water, saline, glycerol, polyethyleneglycol, hyaluronic acid, ethanol, etc. Additionally, auxiliary substances, such as wetting or emulsifying agents, pH buffering substances, and the like, may be present in such vehicles.

For example, intranasal and pulmonary formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

For rectal and urethral suppositories, the vehicle composition will include traditional binders and carriers, such as, cocoa butter (theobroma oil) or other triglycerides, vegetable oils modified by esterification, hydrogenation and/or fractionation, glycerinated gelatin, polyalkaline glycols, mixtures of polyethylene glycols of various molecular weights and fatty acid esters of polyethylene glycol.

For vaginal delivery, the hyaluronic formulations of the present invention can be incorporated in pessary bases, such as those including mixtures of polyethylene triglycerides, or suspended in oils such as corn oil or sesame oil, optionally containing colloidal silica. See, e.g., Richardson et al., *Int. J. Pharm.* (1995) 115:9–15.

For a further discussion of appropriate vehicles to use for particular modes of delivery, see, e.g., *Remington: The Science and Practice of Pharmacy*, Mack Publishing Company, Easton, Pa., 19th edition, 1995. One of skill in the art can readily determine the proper vehicle to use for the particular antigen and site of delivery.

Adjuvants may be used to enhance the effectiveness of the pharmaceutical compositions. The adjuvants may be administered concurrently with the hyaluronic acid formulations of the present invention, e.g., in the same composition or in separate compositions. Alternatively, an adjuvant may be administered prior or subsequent to the hyaluronic acid compositions of the present invention. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PB (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2 etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy) ethylamine (MTP-PE), etc.

The various components of the composition can be present in a wide range of ratios. For example, the hyaluronic acid-antigen and adjuvant components are typically used in a volume ratio of 1:50 to 50:1, preferably 1:10 to 10:1, more preferably from about 1:3 to 3:1, and most preferably about 1:1. However, other ratios may be more appropriate for specific purposes, such as when a particular antigen is both difficult to incorporate into an hyaluronic acid composition and has a low immungenicity, in which case a higher relative amount of the antigen component is required.

The compositions will comprise a "therapeutically effective amount" of the antigen of interest. That is, an amount of antigen will be included in the compositions which will cause the subject to produce a sufficient immunological response in order to prevent, reduce or eliminate symptoms. The exact amount necessary will vary, depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, an effective dose will typically range from about 1 $\mu$g to about 100 mg, more preferably from about 5 $\mu$g to about 1 mg, and most preferably about 10 $\mu$g to about 500 $\mu$g of the antigen delivered per dose.

Once formulated, the compositions of the invention are administered mucosally, using standard techniques. See, e.g., Remington: The Science and Practice of Pharmacy, Mack Publishing Company, Easton, Pa., 19th edition, 1995, for mucosal delivery techniques, including intranasal, pulmonary, vaginal and rectal techniques, as well as European Publication No. 517,565 and Illum et al., J. Controlled Rel. (1994) 29:133–141, for techniques of intranasal administration.

Dosage treatment may be a single dose schedule or a multiple dose schedule. A multiple dose schedule is one in which a primary course of vaccination may be with 1–10 separate doses, followed by other doses given at subsequent time intervals, chosen to maintain and/or reinforce the immune response, for example at 1–4 months for a second dose, and if needed, a subsequent dose(s) after several months. The boost may be with the same formulation given for the primary immune response, or may be with a different formulation that contains the antigen. The dosage regimen will also, at least in part, be determined by the need of the subject and be dependent on the judgment of the practitioner. Furthermore, if prevention of disease is desired, the vaccines are generally administered prior to primary infection with the pathogen of interest. If treatment is desired, e.g., the reduction of symptoms or recurrences, the vaccines are generally administered subsequent to primary infection.

The formulations can be tested in vivo in a number of animal models developed for the study of mucosal delivery. For example, the conscious sheep model is an art-recognized model for testing nasal delivery of substances due to the large nasal cavity, accessibility of the jugular veins for cannulation, as well as the mild tempermant of sheep under experimental conditions. See, e.g., Longenecker et al., J. Pharm. Sci. (1987) 76:351–355 and Illum et al., J. Controlled Rel. (1994) 29:133–141. Sheep can therefore be administered a test substance by briefly sedating the animals to prevent sneezing during administration and inserting an oral/nasal tube with the vaccine in question into the sheep's nostril to a preset depth. The vaccine, generally in powdered, lyophilized form, is then blown into the nasal cavity. Blood samples are then collected from the cannulated jugular vein prior and subsequent to administration. Blood samples can be assayed for antibody titers using standard techniques, known in the art, as described above. Cellular immune responses can also be monitored as described above.

As is readily apparent, the compositions of the present invention are useful for treating and/or preventing a wide variety of diseases and infections caused by viruses, bacteria, parasites and fungi, as well as for stimulating an immune response against a variety of tumor antigens. Not only can the compositions be used therapeutically or prophylactically, as described above, the compositions may also be used in order to prepare antibodies, both polyclonal and monoclonal, for, e.g., diagnostic purposes, as well as for immunopurification of the antigen of interest. If polyclonal antibodies are desired, a selected mammal, (e.g., mouse, rabbit, goat, horse, etc.) is immunized with the compositions of the present invention. The animal is usually boosted 2–6 weeks later with one or more administrations of the antigen. Polyclonal antisera is then obtained from the immunized animal and treated according to known procedures. See, e.g., Jurgens et al. (1985) J. Chrom. 348:363–370.

Monoclonal antibodies are generally prepared using the method of Kohler and Milstein, Nature (1975) 256:495–96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B cells, expressing membrane-bound immunoglobulin specific for the antigen, will bind to the plate, and are not rinsed away with the rest of the suspension. Resulting B cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (as ascites in mice). See, e.g., M. Schreier et al., Hybridoma Techniques (1980); Hammerling et al., Monoclonal Antibodies and T-cell Hybridomas (1981); Kennett et al., Monoclonal Antibodies (1980); see also U.S. Pat. Nos. 4,341,761; 4,399,121; 4,427, 783; 4,444,887; 4,452,570; 4,466,917; 4,472,500, 4,491, 632; and 4,493,890. Panels of monoclonal antibodies produced against the polypeptide of interest can be screened for various properties; i.e., for isotype, epitope, affinity, etc.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation and Use of HYAFF Formulations Including Influenza Antigen

Placebo (Blank) microparticles of HYAFF11 polymer, approximately 100% esterified with benzyl alcohol, were supplied by Fidia Advanced Biopolymers Srl (Abano Terme, Italy). The average size of these microparticles was about 8 microns (with a portion of the size distribution being less than 1 micron and a portion above 10 microns), as determined by a Malvern Mastersizer Instrument.

In order to achieve a dose of 10 μg influenza antigen H3N2 ("HA") (Chiron Vaccines, Sienna, Italy) and 10–25 μg LT-K63 (International Publication No. WO 93/13202), a 1% w/w loading of HA/LT-K63 to microparticles was targeted. To do so, 1 mg of HA and 1 mg of LT-K63, in 84 mM $Na_2HPO_4$, 11 mM $KH_2PO_4$, 82 mM NaCl, was incubated with 100 mg of blank microspheres in PBS at 4° C. for three hours. The suspension was then frozen at −80° C. and freeze-dried overnight.

Actual antigen/adjuvant load was confirmed by hydrolyzing the microparticles and estimating the total protein content by micro-BCA, as described in Sharif and O'Hagan, *Int. J. Pharm.* (1995) 115:259–263. The actual load ranged from about 0.8% to 1.0% w/w antigen/LT-K63 to microparticle.

Prior to immunization, approximately 20 mg of the dried microparticle formulation was suspended in normal saline prior to intranasal delivery to animals. For mice, the formulation was suspended in 50 μl of saline; for guinea pigs the formulation was suspended in 250 μl saline; and for micro pigs, the formulation was suspended in 500 μl.

Balb/C mice were divided into six groups and administered the formulations indicated below intranasally, using a micropipette. Animals were boosted 28 days later.

Group 1 Antigen (HA) alone in saline
Group 2 HA colyophilized with 0.5 mg of HYAFF placebo microparticles
Group 3 HA with LT-K63 (10 μg) in saline
Group 4 HA colyophilized with 0.5 mg of HYAFF placebo microparticles and 10 μg of LT-K63
Group 5 HA with LT-K63 (25 μg) in saline
Group 6 HA colyophilized with 0.5 mg of HYAFF placebo microparticles and 25 μg of LT-K63

Animals were bled on day 42 and anti-HA titers determined by ELISA by estimating the total anti-HA IgG titers in the sample sera. As shown in Table 1, animals administered antigen in combination with HYAFF, both with and without adjuvant, had higher antibody titers than those administered antigen alone. Those administered antigen with HYAFF and adjuvant had the highest titers.

TABLE 1

| Group No. | Formulation | Antigen (HA) | HI Titer |
|---|---|---|---|
| 1 | HA | 10 μg | 80 |
| 2 | HA-HYAFF 0.5 mg | 10 μg | 160 |
| 3 | HA + LT-K63 (10 μg) | 10 μg | 640 |
| 4 | HA-HYAFF 0.5 mg + LT-K63 10 μg | 10 μg | 1280 |
| 5 | HA + LT-K63 (25 μg) | 10 μg | 640 |
| 6 | HA-HYAFF 0.5 mg + LT-K63 25 μg | 10 μg | 2560 |

EXAMPLE 2

Preparation and Use of ACP Formulations Including Influenza Antigen

Auto-crosslinked polysaccharide (ACP) hyaluronic acid gel was obtained from Fidia Advanced Biopolymers Srl (Abano Terme, Italy) and used as shipped. To the gel was added 10 μg of HA and 10–25 μg LT-K63, in an aqueous solution to make a gel-to-water ratio of 1:30.

50 μl of the viscous solution was administered intranasally using a micropipette to three groups of Balb/C mice each with five animals, as shown in Table 2 below. Formulations were administered within 60 minutes of preparation. Animals were boosted 28 days later, bled on day 42 and anti-HA titers determined by ELISA. IgA titers from a nasal wash were also assayed.

As shown in Table 2, animals administered antigen in combination with ACP and adjuvant had higher antibody titers than those administered antigen alone.

TABLE 2

| Groups | Formulation | Serum anti-HA ELISA Titers | IgA Titers in the Nasal Wash |
|---|---|---|---|
| 1 | ACP (1:30) + LT-K63 (25 μg) + HA (10 μg) | 449 +/− 84 | 1836 +/− 630 |
| 2 | LT-K63 (25 μg) + HA (10 μg) | 193 +/− 152 | 808 +/− 161 |
| 3 | HA (10 μg) | 100 +/− 90 | 5.3 +/− 3.5 |

The above study was repeated using the groups of guinea pigs with five animals each. The method used was as described above except that guinea pigs were administered 200 μl of the formulation indicated in Table 3 and boosted twice, once on day 28 and once on day 56. As shown in Table 3, animals administered antigen in combination with ACP and adjuvant had higher antibody titers than those administered antigen alone.

TABLE 3

| Groups | Formulation | Serum Anti-HA ELISA Titers |
|---|---|---|
| 1 | ACP (1:30) + LT-K63 (25 μg) + HA (10 μg) | 1064 +/− 912 |
| 2 | LT-K63 (25 μg) + HA (10 μg) | 571 +/− 423 |
| 3 | HA (10 μg) | 21 +/− 24 |

EXAMPLE 3

Comparison of HYAFF and ACP Formulations

The immunogenicity of the HA antigen in HYAFF and ACP gel was evaluated in micro pigs (Yucatan). 12 pigs were divided into three groups of four pigs each, as shown in Table 4. In order to achieve the proper dose, pigs were administered intranasally using a gauge 16 Teflon catheter, 500 μl of the ACP formulation or 50 mg of the HYAFF formulation. Control pigs were given 500 μl of antigen alone. Pigs were boosted at 28 days and sera collected and assayed for anti-HA serum IgG levels using an ELISA.

As can be seen in Table 4, groups of pigs administered antigen with HYAFF or ACP both had higher titers than pigs administered antigen alone, with pigs administered the HYAFF formulations having the highest titers.

TABLE 4

| Groups | Formulation | Serum Anti-HA ELISA Titers |
|---|---|---|
| 1 | LT-R72 (100 μg) + HA (100 μg) | 505 +/− 183 |
| 2 | LT-R72 (100 μg) + HA (100 μg)-HYAFF | 1919 +/− 602 |
| 3 | LT-R72 (100 μg) + HA (100 μg) + ACP | 871 +/− 155 |

EXAMPLE 4

Comparison of Formulations Delivered Intramuscularly and Intranasally

The ability of the formulations specified in Table 5, delivered either intramuscularly (i.m.) or in intranasally (i.n.), to elicit an immune response, was evaluated in micro pigs (Yucatan). In particular, 12 pigs were divided into three groups of four pigs each, as shown in Table 5. Pigs were immunized with either 25 μg of HA antigen, i.m. (Group 1), 25 μg of HA antigen and 100 μg of LT-K63, i.n. (Group 2), or 25 μg HA with HYAFF microspheres and 100 μg LT-K63, i.n. (Group 3). Pigs were immunized at weeks 0 and 4. Sera and nasal secretions were collected at day 28, 42 and 56 and assayed for anti-HA serum IgG levels and IgA levels using an ELISA.

Figure 2:
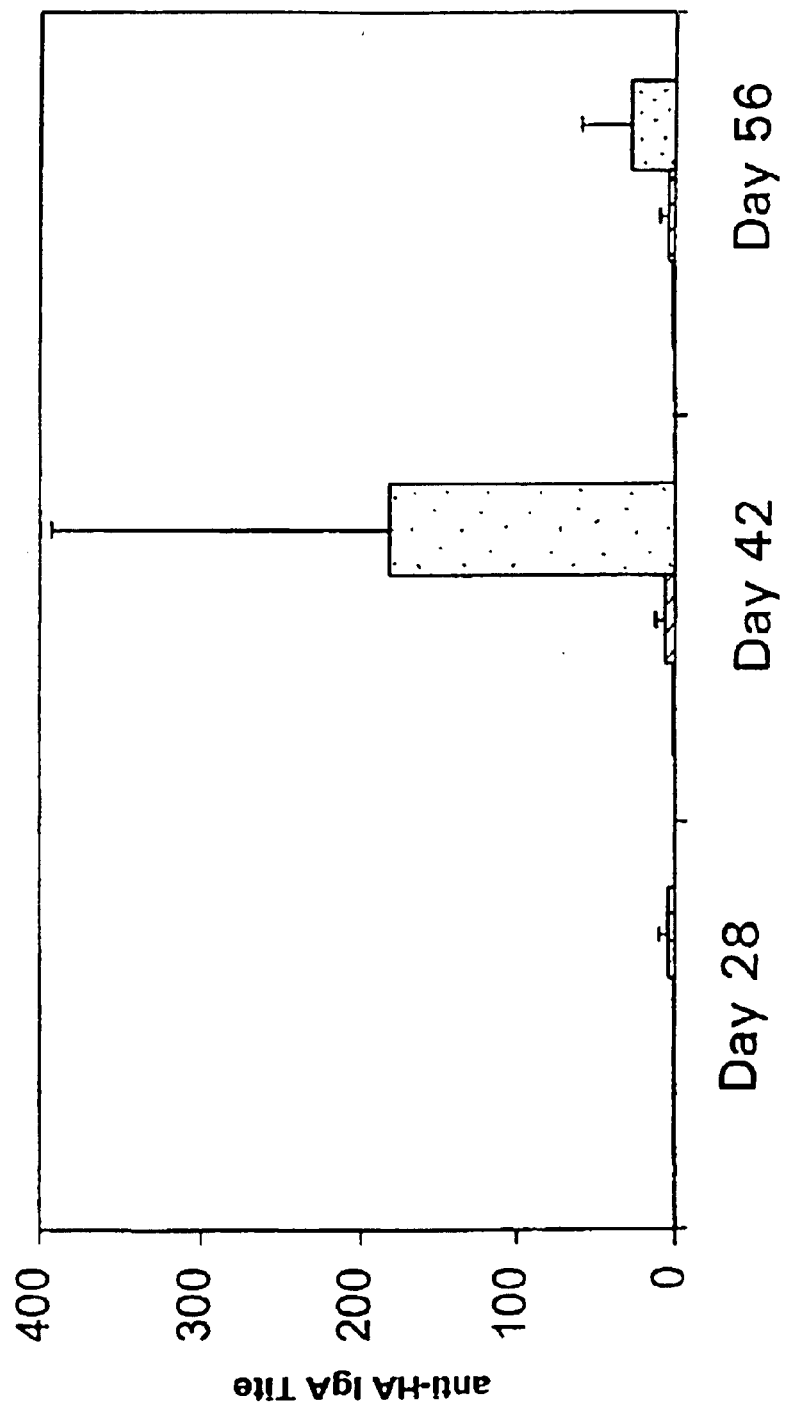
FIG. 2 shows anti-HA IgA titers in pigs administered HA alone intramuscularly (open bars), HA and the adjuvant LT-K63 intranasally (solid bars) and HA with HYAFF microparticles and LT-K63 intranasally (cross-hatched bars).

As can be seen in FIGS. 1 and 2, pigs administered the HYAFF formulation generated a significantly higher response than either the i.m. or i.n. groups lacking HYAFF. The HYAFF formulation also gave a higher HA-specific nasal IgA response. The hemagglutination inhibition (HI) titers (see Table 5), were also the highest in the HYAFF immunized group of animals.

This example shows that intranasal administration or antigen with HYAFF achieves better results than intramuscular administration of antigen alone.

TABLE 5

| Groups | Formulation | Route | Animal No. | Hemagglutination Inhibition Titers |
|---|---|---|---|---|
| 1 | HA Alone | i.m. | 1 | 80 |
|   |   |   | 2 | 640 |
|   |   |   | 3 | 160 |
|   |   |   | 4 | 160 |
| 2 | HA + LTK63 | i.n. | 5 | 40 |
|   |   |   | 6 | 1280 |
|   |   |   | 7 | 320 |
|   |   |   | 8 | 640 |
| 3 | HA + LTK63 + HYAFF | i.n. | 9 | 1280 |
|   |   |   | 10 | 320 |
|   |   |   | 11 | 640 |
|   |   |   | 12 | 2560 |

Accordingly, the use of hyaluronic acid derivatives to deliver vaccine antigens is described. Although preferred embodiments of the subject invention have been described in some detail, it is understood that obvious variations can be made without departing from the spirit and scope of the invention as defined by the appended claims.

We claim:

1. A composition comprising an hyaluronic acid ester polymer in the form of a microsphere, a detoxified mutant of a bacterial ADP-ribosylating toxin, and a selected antigen, wherein said antigen is present in an amount of approximately 0.1% to about 40% (w/w) antigen to hyaluronic acid polymer, and wherein the antigen is not entrapped in the microsphere.

2. The composition of claim 1, wherein said antigen is present in an amount of approximately 2% to about 25% (w/w) antigen to hyaluronic acid polymer.

3. The composition of claim 1, wherein the hyaluronic acid ester is selected from the group consisting of an hyaluronic acid where from about 75% to about 100% of free carboxyl groups are esterified with one or more alkyl groups, and a crosslinked derivative of hyaluronic acid in which about 0.5% to about 20% of the carboxyl groups of the hyaluronic acid polymer are crosslinked to hydroxyl groups of the same or a different hyaluronic acid molecule.

4. The composition of claim 1, wherein the detoxified mutant of a bacterial ADP-ribosylating toxin selected from the group consisting of LT-K63 and LT-R72.

5. The composition of claim 1, wherein the selected antigen is a viral antigen.

6. The composition of claim 5, wherein the selected antigen is an influenza antigen.

7. A composition comprising (a) a microsphere comprised of an hyaluronic acid ester polymer selected from the group consisting of an hyaluronic acid where from about 75% to about 100% of free carboxyl groups are esterified with one or more alkyl groups, and a crosslinked derivative of hyaluronic acid in which about 0.5% to about 20% of the carboxyl groups of the hyaluronic acid polymer are crosslinked to hydroxyl groups of the same or a different hyaluronic acid molecule; (b) a selected antigen adsorbed to the microsphere, wherein said antigen is present in an amount of approximately 2% to about 25% (w/w) antigen to hyaluronic acid polymer; and (c) an immunological adjuvant.

8. A method of making a pharmaceutical composition which comprises combining the composition of claim 1 with a pharmaceutically acceptable mucosal excipient.

9. A method of making a pharmaceutical composition which comprises combining the composition of claim 7 with a pharmaceutically acceptable mucosal excipient.

10. A method of immunization which comprises mucosally administering a therapeutically effective amount of the pharmaceutical composition of claim 8 to a vertebrate subject.

11. A method of immunization which comprises mucosally administering a therapeutically effective amount of the pharmaceutical composition of claim 9 to a vertebrate subject.

12. The method of claim 10 wherein the administering is done intranasally.

13. The method of claim 11 wherein the administering is done intranasally.

14. The composition of claim 1, wherein the microsphere is a nanosphere.

15. The composition of claim 7, wherein the microsphere is a nanosphere.

* * * * *